(12) United States Patent
Kabra

(10) Patent No.: US 7,727,549 B2
(45) Date of Patent: Jun. 1, 2010

(54) PHARMACEUTICAL COMPOSITIONS FOR OTIC USE

(75) Inventor: Bhagwati P. Kabra, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 1418 days.

(21) Appl. No.: 10/609,975

(22) Filed: Jun. 30, 2003

(65) Prior Publication Data

US 2004/0014819 A1 Jan. 22, 2004

Related U.S. Application Data

(60) Provisional application No. 60/395,958, filed on Jul. 15, 2002.

(51) Int. Cl.
*A61K 9/20* (2006.01)
(52) U.S. Cl. ..................... 424/465; 424/400
(58) Field of Classification Search ............ None
See application file for complete search history.

(56) References Cited

U.S. PATENT DOCUMENTS

| | | | |
|---|---|---|---|
| 4,344,968 A * | 8/1982 | Aoda et al. ............ 514/8 |
| 4,786,495 A * | 11/1988 | Bird et al. ............ 424/456 |
| 4,880,636 A | 11/1989 | Franz |
| 5,100,918 A * | 3/1992 | Sunshine et al. ........ 514/557 |
| 5,433,951 A * | 7/1995 | Serajuddin et al. ....... 424/486 |
| 5,597,560 A | 1/1997 | Bergamini et al. ...... 424/78.04 |
| 5,618,800 A | 4/1997 | Kabra et al. ............ 514/57 |
| 5,736,152 A | 4/1998 | Dunn ................ 424/426 |
| 5,747,061 A | 5/1998 | Amselem et al. ......... 424/427 |
| 5,753,269 A | 5/1998 | Groh et al. ............ 424/618 |
| 5,891,476 A | 4/1999 | Reo et al. |
| 5,942,508 A * | 8/1999 | Sawa ................ 514/235.8 |
| 6,174,878 B1 | 1/2001 | Gamache et al. ....... 514/211.12 |
| 6,284,804 B1 | 9/2001 | Singh et al. .......... 514/772.4 |
| 6,316,011 B1 | 11/2001 | Ron et al. ............ 424/401 |
| 6,346,272 B1 | 2/2002 | Viegas et al. .......... 424/486 |
| 6,359,016 B2 | 3/2002 | Singh et al. .......... 514/772.4 |
| 6,525,214 B1 * | 2/2003 | Armitage et al. ........ 562/401 |
| 6,645,506 B1 * | 11/2003 | Farmer .............. 424/260.1 |

FOREIGN PATENT DOCUMENTS

| EP | 0 279 519 A1 | 8/1988 |
|---|---|---|
| EP | 0 420 056 A2 | 9/1990 |
| EP | 0 940 138 A1 | 9/1999 |
| WO | WO 00/18388 | 4/2000 |
| WO | WO 01/22936 A1 | 4/2001 |

OTHER PUBLICATIONS

Brown et al. "Chemistry the Central Science" 6th ed. 1993.*
Hamdanl et al., "Physical and thermal characterisation of Precirole® and Comptirol® as lipophlic glycerides used for the preparation of controlled-release matrix pellets," *International J. of Pharmaceutics*, vol. 260, pp. 47-57 (2003).
Glycerol Distearate, *European Pharmacopeia*, vol. 5.0, pp. 1674-1675, 2005.
Glyceryl Distearate, *US Pharmacopeia*, pp. 3341-3342, 2007.
Glyceryl Monostearate, *Japanese Pharmacopeia*, pp. 931, 1996.

* cited by examiner

*Primary Examiner*—Eric E. Silverman
(74) *Attorney, Agent, or Firm*—Scott A. Chapple

(57) ABSTRACT

Otic compositions are disclosed. The compositions contain an otic drug and a carrier comprising a low molecular weight compound. The compositions do not drain out of the ear after administration.

9 Claims, No Drawings

PHARMACEUTICAL COMPOSITIONS FOR OTIC USE

This application claims priority to U.S. Provisional Application, U.S. Ser. No. 60/395,958, filed Jul. 15, 2002.

BACKGROUND OF THE INVENTION

This invention relates to pharmaceutical compositions. In particular, this invention relates to the use of carriers containing low molecular weight compounds that reversibly change from solid to liquid at approximately 32-37° C. in compositions for otic use.

Otic compositions designed for topical application to the external ear are typically aqueous compositions. Such compositions can be formulated as simple aqueous solutions or suspensions. Alternatively, such compositions may be formulated as an oil-in-water emulsion, such as those described in U.S. Pat. No. 5,753,269. Still another possibility for use in topical otic compositions is a polymeric ingredient. See, for example, U.S. Pat. No. 5,747,061, which describes suspension formulations of the steroid loteprednol etabonate for treating the ear, eye or nose. Gel-forming compositions and gel compositions are also used for delivering otic drugs. See, for example, U.S. Pat. No. 6,316,011, which describes certain thermal responsive hydrogels suitable for administering a pharmaceutical agent across otic membranes. See also U.S. Pat. No. 6,346,272, which describes thermo-irreversible gel vehicles that may be used to deliver otic drugs, wherein the vehicle contains a polyoxyalkylene polymer and an ionic polysaccharide and the vehicle is a liquid before administration to the body and transform, upon contact with the body, into "a semi-solid gel having a very high viscosity" (Col. 2, line 64-Col. 3, line 1). The compositions of the '272 patent may be formulated as homogeneous, polyphase systems and, in addition to the polyoxyalkylene polymer and the ionic polysaccharide, optionally contain "such additives as water insoluble high molecular weight fatty acids and alcohols, fixed oils, volatile oils and waxes, mono-, di-, and triglycerides, and synthetic, water insoluble polymers without altering the functionality of the system" (Col. 3, lines 16-21).

SUMMARY OF THE INVENTION

The present invention provides otic compositions comprising a pharmaceutical drug and a carrier containing one or more low molecular weight compounds. The carrier is a solid or semi-solid at temperatures $\leq 32°$ C., but liquid at temperatures $\geq 37°$ C. The compositions reversibly change from solid to liquid at a temperature of 32-37° C.

DETAILED DESCRIPTION OF THE INVENTION

Unless indicated otherwise, all ingredient amounts expressed in percentage terms are presented as % w/w.

The compositions of the present invention comprise an optically acceptable pharmaceutical drug and a carrier comprising one or more compounds having a molecular weight of 150-4000, wherein the compounds are of the formula:

$$H_2C-R^2$$
$$|$$
$$R^1$$
(I)

wherein $R^1$ is $-H$, $-OH$, $-COOH$, $-C_nH_{2n+1-2m}$, $-COOC_nH_{2n+1-2m}$, $-COO(CH_2CH_2O)_nCH_2CH_2OH$, $-CH_2R^3$, or

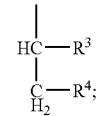

$R^2$, $R^3$ and $R^4$ are independently $-H$, $-OH$, $-COOH$, $-C_nH_{2n+1-2m}$, $-OOCC_nH_{2n+1-2m}$, $-COOC_nH_{2n+1-2m}$, $-COO(CH_2CH_2O)_nCH_2CH_2OH$, $-C_nH_{2n+1-2m}COO(CH_2CH_2O)_nCH_2CH_2OH$, $-OOCC_nH_{2n+1-2m}COOC_nH_{2n'+1-2m'}$, $-COO^-Na^+$, $-COO^-K^+$, $-SO_3H$, $-SO_3^-Na^+$, $-SO_3^-K^+$, $-NH_2$, $-Cl$,

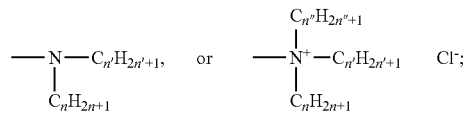

n, n' and n" are independently 0-50; and
m, m' and m" are independently 0-10.

In a preferred embodiment, the compositions do not contain any polymeric ingredient and the carrier consists essentially of one or more compounds of formula (I). Preferably, the molecular weight of the low molecular weight compounds of formula (I) used in the compositions present invention is $\leq 2000$, and most preferably $\leq 1000$. If the carrier of the present invention contains only one compound of formula (I), then the compound must have a melting point in the range of 32-37° C. If the carrier contains two or more compounds of formula (I), it is only necessary that the mixture of the two or more compounds of formula (I) has a melting point in the range of 32-37° C.

Preferred are the compounds of formula (I) wherein $R^1$ is, $-C_nH_{2n+1-2m}$, $-COOC_nH_{2n+1-2m}$, $-COO(CH_2CH_2O)_nCH_2CH_2OH$, $-CH_2R^3$, or

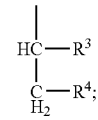

$R^2$, $R^3$ and $R^4$ are independently $-H$, $-OH$, $-COOH$, $-C_nH_{2n+1-2m}$, $-OOCC_nH_{2n+1-2m}$, $-COOC_nH_{2n+1-2m}$, $-COO(CH_2CH_2O)_nCH_2CH_2OH$, $-C_nH_{2n+1-2m}COO(CH_2CH_2O)_nCH_2CH_2OH$, or $-OOCC_nH_{2n+1-2m}COOC_nH_{2n'+1-2m'}$;

n, n' and n" are independently 0-40; and
m, m' and m" are independently 0-5.

Most preferred are the compounds of formula (I) wherein $R^1$ is

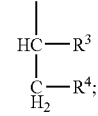

$R^2$, $R^3$ and $R^4$ are independently —H, —OH, —COOH, —$C_nH_{2n+1-2m}$, or —$OOCC_nH_{2n+1-2m}$;

n, n' and n" are independently 0-30; and m, m' and m" are independently 0-3.

The compounds of the present invention can be made by methods known in the art and many such compounds are commercially available. For example, commercial suppliers include NuChek Prep (Elysian, Minn.), Quest International (Hoffman Estates, Ill.), which produces such compounds under the Myvace® brand, and Gattefossa (Saint-Priest, France), which produces such compounds under the Gelucire®, Suppocire™, Ovucire™, and Monosteol® brands. Suitable compounds include, but are not limited to, the following commercially available products.

propylene glycol mono- and diesters of stearic and palmitic acid (Monosteol®);

glyceryl esters of saturated $C_8$-$C_{18}$ saturated fatty acid esters (Gelucire® 33/01);

Suppocire AIM;

Suppocire AM;

Suppocire BM;

Suppocire NAI 25; and

Suppocire NAL

The compositions of the present invention comprise one or more of the compounds of formula (I) in a total concentration of at least 10%, preferably at least 30%, and most preferably at least 50%.

The compositions of the present invention comprise a pharmaceutically effective amount of an otic drug. If necessary or desired, more than one drug can be included in the composition of the present invention. Many types of otic drugs are known, including but not limited to: anti-infective agents including quinolones such as ciprofloxacin, and aminoglycosides such as tobramycin and gentamicin; and non-steroidal and steroidal anti-inflammatory agents, such as suprofen, diclofenac, ketorolac, rimexolone, dexamethasone, hydrocortisone and tetrahydrocortisol. Anti-pain otic drugs are also known, such as those disclosed in U.S. Pat. No. 6,174,878. The otic drug may be present in the form of a pharmaceutically acceptable salt. Compositions of the present invention may also include combinations of otic drugs. The total amount of drug contained in the implant compositions of the present invention is preferably not greater than 50%.

In addition to the compound of formula (I) and an otic drug, the compositions of the present invention optionally comprise one or more excipients. Many excipients for pharmaceutical compositions are known. Examples of suitable excipients include, but are not limited to surfactants and other solubilizing agents, preservatives, and stabilizers.

Suitable surfactants include tyloxapol, polysorbate 20, polysorbate 60, and polysorbate 80 surfactants. A preferred surfactant is polysorbate 80.

Suitable stabilizers include chelating agents, such as edetate disodium, and antioxidants, such as ascorbic acid and citric acid.

The compositions may be fashioned into a shape suitable for insertion into the ear. For example, such shapes include, but are not limited to cylindrical, conical and spherical shapes. Alternatively, the compositions may be dropped, injected, deposited, or sprayed into the ear. The compositions of the present invention are administered to the external ear, including the ear canal. In one embodiment, the compositions of the present invention are warmed to a temperature above 35° C. and administered topically into the ear canal as ear drops or injected through a cannula into the ear canal.

The present invention is also directed toward a method of delivering an otic drug to the ear of a patient wherein the method comprises administering to the ear a composition containing the otic drug and a carrier comprising one or more low molecular weight compounds of formula (I). According to this method, the compositions do not drain out of the ear because they are solid or semi-solid at the temperature of the external ear. On the other hand, the compositions easily allow the drug to diffuse or escape the carrier because the carrier is liquid at 37° C., the average temperature of the inner ear and it is generally easier for a drug to escape a liquid than a solid.

The following examples are intended to illustrate, but not limit, the present invention.

EXAMPLE 1

Composition Containing Dexamethasone

A 95:4:1 (weight basis) composition of Monosteol®, dexamethasone, and polysorbate 80 is heated to melt the Monosteol® and mixed. 1×2 mm cylindrical pellets are made by cooling the mixture in a cylindrical mold. Monosteol® contains, according to its manufacturer, no less than 90% total of the following two ingredients:

propylene glycol monostearate ($C_{21}H_{42}O_3$):

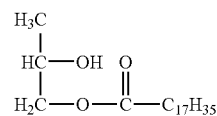

propylene glycol monopalmitate ($C_{19}H_{38}O_3$)

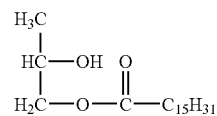

EXAMPLE 2

Composition containing Dexamethasone and Ciprofloxacin

A 82:4:12:2 (weight basis) composition of Monosteol®, dexamethasone, ciprofloxacin hydrochloride and polysorbate 80 is heated to melt the Monosteol® and mixed. 1×2 mm cylindrical pellets are made by cooling the mixture in a cylindrical mold.

EXAMPLE 3

Dexamethasone Gelucire® 33/01 Particles

A 95:4:1 (weight basis) composition of dexamethasone, Gelucire® 33/01 and polysorbate 80 is heated to melt the Gelucire® 33/01 and mixed. This mixture is then spray dried to produce particles for incorporation into an otic spray composition.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of delivering an otic drug to the ear comprising the steps of
(a) preparing an otic composition comprising the otic drug and a carrier, wherein the carrier comprises a low molecular weight compound having a molecular weight of 150-4000, the carrier reversibly changes from solid to liquid at a temperature of 32-37° C., and the low molecular weight compound has the formula:

(I)

wherein $R^1$ is —H, —OH, —COOH, $C_nH_{2n+1-2m}$, $COOC_nH_{2n+1-2m}$, —COO(CH$_2$CH$_2$O)$_n$CH$_2$CH$_2$OH, —CH$_2R^3$, or

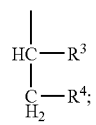

$R^2$, $R^3$ and $R^4$ are independently —H, —OH, —COOH, —$C_nH_{2n+1-2m}$, —OOC$C_nH_{2n+1-2m}$, —COO$C_nH_{2n+1-2m}$, —COO(CH$_2$CH$_2$O)$_n$CH$_2$CH$_2$OH, —$C_nH_{2n+1-2m}$COO(CH$_2$CH$_2$O)$_n$CH$_2$CH$_2$OH, —OOC$C_nH_{2n+1-2m}$COO$C_{n'}H_{2n'+1-2m'}$, —COO$^-$Na$^+$, —COO$^-$K$^+$, —SO$_3$H, —SO$_3^-$Na$^+$, —SO$_3^-$K$^+$, —NH$_2$, —Cl,

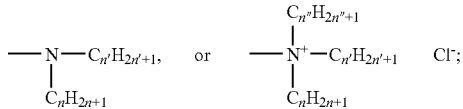

n, n' and n" are independently 0-50; and
m, m' and m" are independently 0-10,
and
(b) inserting the composition prepared in step (a) in the ear canal.

2. The method of claim 1, wherein the composition prepared in step (a) is dropped, injected, deposited, or sprayed into the external ear.

3. The method of claim 2 wherein the composition prepared in step (a) is warmed to a temperature above 32° C. and administered topically or locally as an ear drop or through a cannula.

4. The method of claim 1 wherein the composition prepared in step (a) does not contain any polymeric ingredient and the carrier consists essentially of one or more low molecular weight compounds of formula (I).

5. The method of claim 1 wherein the low molecular weight compound of formula (I) has a molecular weight ±2000.

6. The method of claim 1 wherein
$R^1$ is, —$C_nH_{2n+1-2m}$, —COO$C_nH_{2n+1-2m}$, —COO(CH$_2$CH$_2$O)$_n$CH$_2$CH$_2$OH, —CH$_2R^3$, or

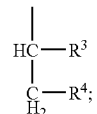

$R^2$, $R^3$ and $R^4$ are independently —H, —OH, —COOH, —$C_nH_{2n+1-2m}$, OOC$C_nH_{2n+1-2m}$, —COO$C_nH_{2n+1-2m}$, —COO(CH$_2$CH$_2$O)$_n$CH$_2$CH$_2$OH, —$C_nH_{2n+1-2m}$COO(CH$_2$CH$_2$O)$_n$CH$_2$CH$_2$OH, or —OOC$C_nH_{2n+1-2m}$COO$C_{n'}H_{2n'+1-2m'}$;
n, n' and n" are independently 0-40; and
m, m' and m" are independently 0-5.

7. The method of claim 6 wherein
$R^1$ is

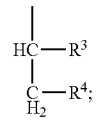

$R^2$, $R^3$ and $R^4$ are independently —H, —OH, —COOH, —$C_nH_{2n+1-2m}$, or —OOC$C_nH_{2n-1-2m}$;
n, n' and n" are independently 0-30; and
m, m' and m" are independently 0-3.

8. The method of claim 1 wherein the total concentration of the low molecular weight compound of formula (I) in the composition prepared in step (a) is at least 10% (w/w).

9. The method of claim 1 wherein the otic drug is one or more compounds selected from the group consisting of anti-infective agents; non-steroidal anti-inflammatory agents; steroidal anti-inflammatory agents; and anti-pain agents.

* * * * *